United States Patent [19]

Mrowca

[11] 4,064,104
[45] Dec. 20, 1977

[54] PHOSPHINE OXIDE FLAME RETARDANTS

[75] Inventor: Joseph J. Mrowca, Wilmington, Del.

[73] Assignee: E. I. Du Pont de Nemours and Company, Wilmington, Del.

[21] Appl. No.: 741,723

[22] Filed: Nov. 15, 1976

Related U.S. Application Data

[60] Division of Ser. No. 552,868, Feb. 25, 1975, abandoned, which is a continuation-in-part of Ser. No. 416,597, Nov. 16, 1973, Pat. No. 3,895,074.

[51] Int. Cl.² ............................................. C08K 5/16
[52] U.S. Cl. ..................... 260/45.9 NP; 260/45.9 NC; 260/45.7 P; 260/456 P; 260/457; 260/556 A
[58] Field of Search ................... 260/606.5 P; 260/45.9 NC, 45.9 NP, 45.7 P, 45.6 P, 457, 556 A, 606.5 P

[56] References Cited

U.S. PATENT DOCUMENTS 3,895,074  7/1975  Mrowca ................. 260/606.5 P
3,975,447  8/1976  Knoth, Jr. et al. ........ 260/606.5 P

OTHER PUBLICATIONS

Dorken, Chem. Berichte (1888), 21, pp. 1505–1515.
Horner, Chem. Berichte (1962), 95, pp. 581–601.

*Primary Examiner*—Melvyn I. Marquis
*Attorney, Agent, or Firm*—Anthony P. Mentis

[57] ABSTRACT

Aromatic phosphine oxide compounds are useful as flame retardants in synthetic polymers and textiles. Exemplary is 2,4,6-trimethylmesitylylenetris(diphenylphosphine oxide).

6 Claims, No Drawings

PHOSPHINE OXIDE FLAME RETARDANTS

RELATED APPLICATION

This is a division of application Ser. No. 552,868, filed Feb. 25, 1975, now abandoned, which in turn is a continuation-in-part of application Ser. No. 416,597 filed Nov. 16, 1973 now U.S. Pat. No. 3,895,074.

BACKGROUND OF THE INVENTION

1. Field of Invention

This invention is concerned with new classes of phosphorus-containing compounds which are useful as flame-retardants for polymers, and particularly for textiles.

2. Prior Art

Kokai, Japanese 73 04, 451 to Asahi Denko Co., Chem. Abs. 79, 5457 v (1973), describes certain phosphine oxide compounds which are not the same as the instant compounds.

U.S. Pat. No. 3,370,030 discloses a flame-retardant composition comprising two critical components: a particular kind of phosphine oxide compound and a chlorinated hydrocarbon material such as chlorinated biphenyl.

U.S. Pat. No. 3,681,281 discloses a flame-retardant composition comprising a tertiary phosphine oxide such as xylylenebis(diphenylphosphine oxide).

DESCRIPTION OF THE INVENTION

The new flame-retardant compounds have the formulas

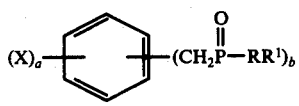

(I)

wherein
- R and $R^1$, individually, are alkyl, aryl or aralkyl, each of up to 10 carbon atoms having up to five chlorine, bromine or fluorine atoms;
- X is chlorine, bromine, OR, SR, SOR, $SO_2R$, $SO_2NH_2$, $SO_2NHR$ or $SO_2NR_2$, R being as defined above;
- $a$ is 1 to 4;
- $b$ is 2 to 5; and
- $a + b$ is 3 to 6; and

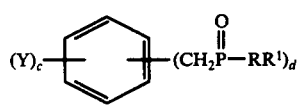

(II)

wherein
- R and $R^1$ are defined as above;
- Y is alkyl of 1 to 6 carbons;
- $c$ is 0 to 3;
- $d$ is 3 to 6; and
- $c + d$ is 3 to 6.

In the compounds of formula I, preferred flame-retardant properties coupled with compatibility with the substrate and high temperature resistance are found in the compounds where at least one of R and $R^1$ is phenyl, X is chlorine or bromine and $a$ is 2 to 4. When X is other than halogen, $a$ is generally 1 to 2.

The compounds of formula II which have the highest phosphorus content impart maximum flame-retardant properties for a minimum loading of the flame-retardant agent in the polymer. A preferred group are the compounds in which $c$ is 0.

The phosphine oxides of this invention are prepared by Arbuzov reactions of halomethyl-substituted aromatics with disubstituted phosphinites as defined in the following reactions A and B:

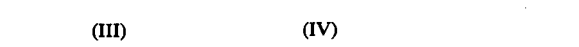

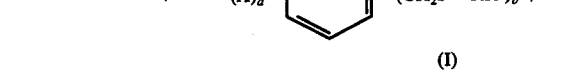

where Z is chlorine or bromine, $R^2$ is alkyl of up to 8 carbon atoms, and X, R, $R^1$, $a$ and $b$ are as previously indicated.

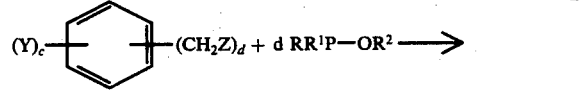

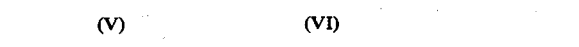

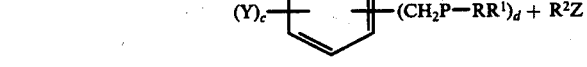

where all of the letters are as previously indicated.

The processes can be run with or without solvent. Without solvent, the reactants can be mixed and then heated to reaction temperature or, alternatively, the halomethyl-substituted aromatic can be heated to reaction temperature and the phosphinite added slowly to it. Suitable inert solvents for the reactions include hydrocarbons, halogenated hydrocarbons, halocarbons, nitriles, ethers, ketones, carboxamides, and phosphorus amides. Preferred solvents are inert polar compounds with boiling points about 110°–200°. Examples of preferred solvents are chlorobenzene, o- and m-dichlorobenzene, benzonitrile, anisole, o- and m-xylene, and toluene.

The reaction temperature ranges are 25°–300° C., with 110°–200° C being preferred.

The reaction times range from about 5 minutes to about 24 hours, with 1 to 5 hours being preferred.

The reactions are advantageously conducted in the substantial absence of air and moisture.

SPECIFIC EMBODIMENTS OF THE INVENTION

The following are illustrative examples of the invention in which all parts are by weight and all temperatures are in degrees Centigrade unless otherwise stated.

EXAMPLE 1

2,4,5,6-Tetrabromo-1,3-xylylenebis(diphenylphosphine Oxide)

X = Br;
a = 4;
b = 2;
R = R¹ = C₆H₅.

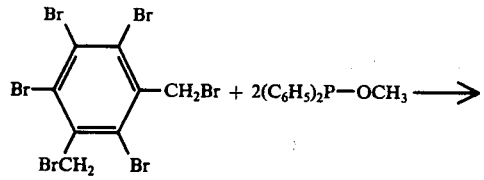

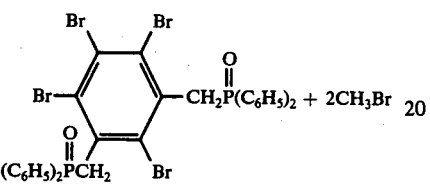

To a stirred, refluxing mixture of 10.00 g of alpha,alpha',2,4,5,6-hexabromo-m-xylene in 100 ml of o-dichlorobenzene under nitrogen was added dropwise a solution of 15.00 g of methyl diphenylphosphinite in 50 ml of o-dichlorobenzene. After the addition was complete, the mixture was refluxed for 5 hrs and cooled. The white solid was filtered, washed with benzene and hexane, and recrystallized from dimethylsulfoxide to give 7.36 g of 2,4,5,6-tetrabromo-1,3-xylylenebis(diphenylphosphine oxide) as white crystals, m.p. 251°–254°.

Anal. Calcd for $C_{32}H_{24}Br_4O_2P_2$: C, 46.75; H, 2.94; P, 7.54. Found: C, 46.54; H, 3.11; P, 7.32.

EXAMPLE 2

2,5-Dibromo-1,4-xylylenebis(diphenylphosphine oxide)

X = Br
a = 2
b = 2
R = R¹ = C₆H₅

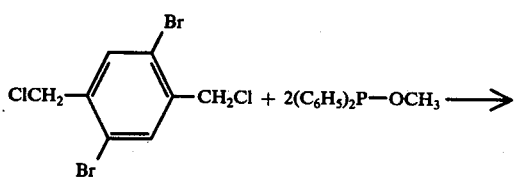

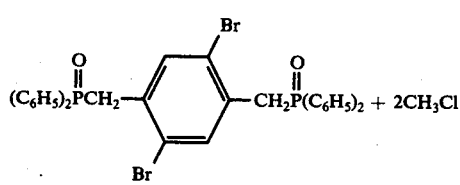

To a stirred, refluxing mixture of 10.00 g of 1,4-bis(-chloromethyl)-2,5-dibromobenzene in 150 ml of o-dichlorobenzene under N₂ was added dropwise a solution of 15.00 g of methyl diphenylphosphinite in 50 ml of o-dichlorobenzene. After the addition was complete, the mixture was refluxed for 5 hrs and cooled. The white solid was filtered, washed with benzene and hexane, and dried at 100° and 0.1 mm for 18 hrs to give 19.10 g of 2,5-dibromo-1,4-xylylenebis(diphenylphosphine oxide), m.p. 301°–303°.

Anal. Calcd for $C_{32}H_{26}Br_2O_2P_2$: C, 57.86; H, 3.95. Found: C, 58.32; H, 4.17; C, 57.96; H, 3.87.

EXAMPLE 3

2,3,5,6-Tetrabromo-1,4-xylylenebis(diphenylphosphine oxide)

X = Br
a = 4
b = 2
R = R¹ = C₆H₅

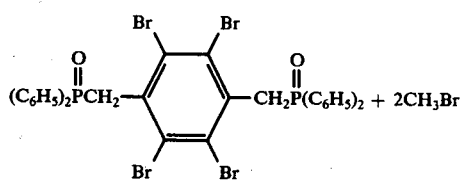

To a stirred, refluxing mixture of 20.00 g of alpha,alpha',2,3,5,6-hexabromo-p-xylene and 200 ml of o-dichlorobenzene under nitrogen was added dropwise a solution of 30.00 g of methyl diphenylphosphinite in 100 ml of o-dichlorobenzene. After the addition was complete, the mixture was refluxed for 3.5 hrs and cooled. The white crystals were filtered, washed with benzene and hexane, and recrystallized from 600 ml of o-dichlorobenzene to give 23.20 g of 2,3,5,6-tetrabromo-1,4-xylylenebis(diphenylphosphine oxide), dec. 310° with melting at 325°–326°.

Anal. Calcd for $C_{32}H_{24}Br_4O_2P_2$: C, 46.75; H, 2.94. Found: C, 46.92; H, 3.21.

EXAMPLE 4

2,3,5,6-Tetrachloro-1,4-xylylenebis(diphenylphosphine oxide)

X = Cl
a = 4
b = 2
R = R¹ = C₆H₅

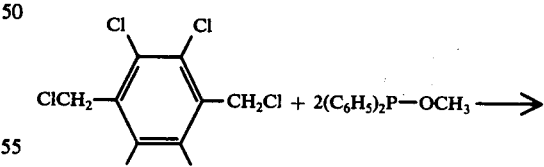

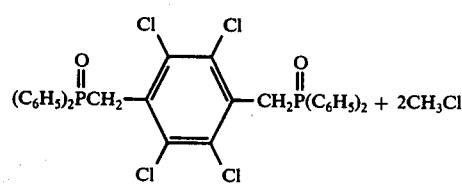

To a stirred, refluxing mixture of 10.00 g of alpha,alpha',2,3,5,6-hexachloro-p-xylene in 150 ml of o-dichlorobenzene under nitrogen was added a solution of 20.00 g of methyl diphenylphosphinite in 50 ml of o- dichlorobenzene. After the addition was complete, the mixture was refluxed for 5 hrs and cooled. The white solid was filtered, washed with benzene and hexane, and recrystallized from 750 ml of o-dichlorobenzene to give 18.50 g of 2,3,5,6-tetrachloro-1,4-xylylenebis(diphenylphosphine oxide) as white crystals, m.p. 339°–341° dec.

Anal. Calcd for $C_{32}H_{24}Cl_4O_2P_2$: C, 59.65; H, 3.76; P, 9.62; Cl, 22.01. Found: C, 59.86; H, 3.89; P, 9.67; Cl, 22.17.

EXAMPLE 5

2,4,5,6-Tetrachloro-1,3-xylylenebis(diphenylphosphine oxide)

X = Cl
a = 4
b = 2
R = R¹ = $C_6H_5$

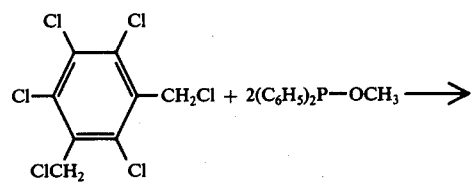

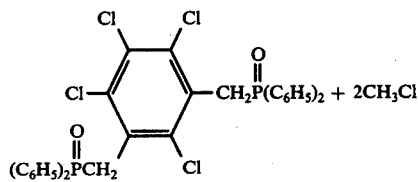

To a stirred, refluxing mixture of 20.00 g of alpha,alpha',2,4,5,6-hexachloro-m-xylene in 300 ml of o-dichlorobenzene under nitrogen was added dropwise 40.00 g of methyl diphenylphosphinite. After the addition was complete, the mixture was refluxed 4 hrs and cooled. The white solid was filtered, washed with benzene and hexane, and recrystallized from 100 ml of chlorobenzene to give 16.78 g of 2,4,5,6-tetrachloro-1,3-xylylenebis(diphenylphosphine oxide) as white crystals, m.p. 228°–231°.

Anal. Calcd for $C_{32}H_{24}Cl_4O_2P_2$: C, 59.65; H, 3.75. Found: C, 59.49; H, 3.85.

The filtrate from the reaction mixture deposited more product as the benzene and hexane washes were mixed with it. The white solid was filtered, washed with hexane, and recrystallized from 50 ml of chlorobenzene to give 6.81 g of additional product, m.p. 228°–231°.

EXAMPLE 6

2-Methoxy-5-methylthio-1,4-xylylenebis(diphenylphosphine oxide)

X = $OCH_3$; $SCH_3$
a = 2
b = 2
R = R¹ = $C_6H_5$

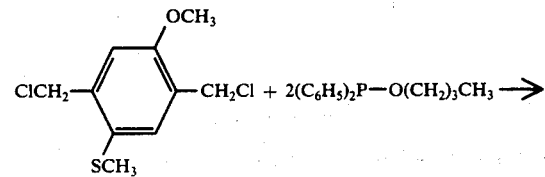

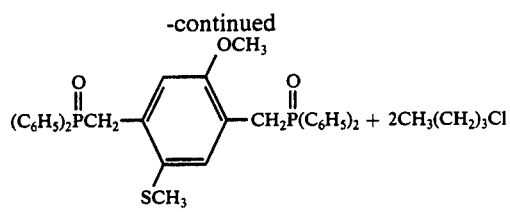

To a stirred, refluxing mixture of 2.50 g of 2-methoxy-5-methylthio-1,4-bis(chloromethyl)benzene in 50 ml of o-dichlorobenzene under nitrogen was added dropwise 6.00 g of n-butyl diphenylphosphinite. After the addition was complete, the mixture was refluxed for 3 hrs and cooled. The white solid was filtered, washed with benzene and hexane, and dried at 150° and 0.1 mm to give 5.31 g of 2-methoxy-5-methylthio-1,4-xylylenebis(diphenylphosphine oxide), m.p. 286°–288°.

Anal. Calcd for $C_{34}H_{32}O_3P_2S$: C, 70.09; H, 5.54. Found: C, 70.32; H, 5.69.

EXAMPLE 7

2-Methoxy-5-methylsulfonyl-1,4-xylylenebis(diphenylphosphine) oxide)

X = $OCH_3$; $SO_2CH_3$
a = 2
b = 2
R = R¹ = $C_6H_5$

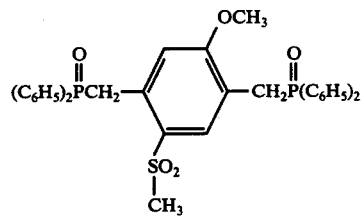

To a stirred solution of 1.75 g of 2-methoxy-5-methylthio-1,4-xylylenebis(diphenylphosphine oxide) in 50 ml of acetic acid at 70° was added dropwise 1.80 g of 30% hydrogen peroxide. After the addition was complete, the mixture was heated at 70° for 3 hrs and then stirred for 18 hrs at room temperature. Water was added and the mixture was cooled. The resulting white precipitate was filtered, washed with water, and recrystallized from 50 ml of chlorobenzene to give 0.92 g of 2-methoxy-5-methylsulfonyl-1,4-xylylenebis(diphenylphosphine oxide) as white crystals, m.p. 285.0°–286.5°.

Anal. Calcd for $C_{34}H_{32}O_5P_2S$: C, 66.44; H, 5.25. Found: C, 66.63; H, 5.50.

EXAMPLE 8

2,4,6-Trimethyl-mesitylylenetris(diphenylphosphine oxide)

X = $CH_3$
a = 3
b = 3
R = R¹ = $C_6H_5$

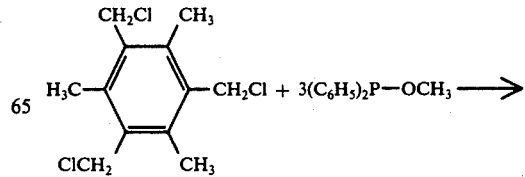

-continued

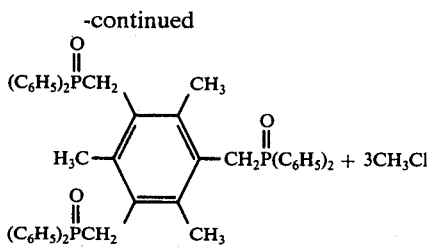

To a stirred, refluxing mixture of 5.00 g of 2,4,6-tris(-chloromethyl)mesitylene in 150 ml of o-dichlorobenzene under nitrogen was added dropwise a solution of 17.00 g of methyl diphenylphosphinite in 50 ml of o-dichlorobenzene. After the addition was complete, the mixture was refluxed for 5 hrs and cooled. The white solid was filtered, washed with benzene and hexane, and dried at 150° and 0.1 mm for 18 hrs to give 12.50 g of 2,4,6-trimethyl-mesitylylene-tris(diphenylphosphine oxide), m.p. 275°–278°.

Anal. Calcd for $C_{48}H_{45}O_3P_3$: C, 75.58; H, 5.95; P, 12.18. Found: C, 75.18; H, 5.94; P, 12.56.

Disubstituted phosphinites which can be used are commercially available or can be prepared by reacting a disubstituted phosphinous chloride with a hydroxy compound, $R^2OH$, in the presence of a tertiary amine such as pyridine or triethylamine according to the reaction:

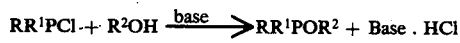

where R, $R^1$ and $R^2$ are as previously stated. Thus, by use of known phosphinous chlorides in the above reaction, useful disubstituted phosphinites, $RR^1POR^2$, are prepared and include those shown in Table I.

Table I
---
$(C_6H_5)_2PO-n-C_8H_{17}$
$(C_6H_5CH_2)_2PO-n-C_2H_5$
$(p-ClC_6H_4)_2PO-n-C_4H_9$
$(n-C_5H_{11})_2PO-n-C_5H_{11}$
$(p-ClC_6H_4)(C_2H_5)POC_2H_5$
$(CH_3)(C_2H_5)POCH_3$
$(\alpha-C_{10}H_7)_2POCH_3$
$(n-C_8H_{17})_2POCH_3$
$(C_6H_5CH_2CH_2)_2POCH_3$
$(p-BrC_6H_4)(C_6H_5)POCH_3$
$(p-FC_6H_4)_2POCH_3$
$(C_6F_5)_2POCH_3$ Additional halomethyl substituted aromatic compounds II which can be used include the benzenesulfonamides where X is $-SO_2NH_2$ and which have 2 to 4 $CH_2Hal$ groups attached to the benzenoid ring. These compounds may be prepared by using N-bromosuccinimide (NBS) as in the reaction:

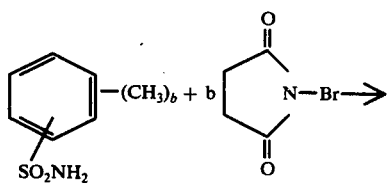

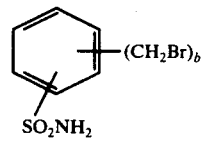

Suitable starting methyl benzenesulfonamides, where b is 2-4, have been described. N,N-disubstituted benzenesulfonamides are also readily available, e.g.,

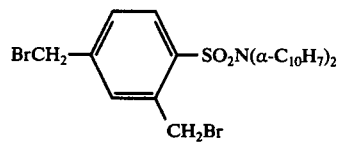

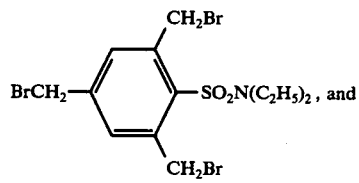

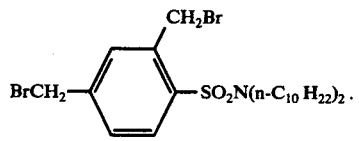

Reaction of these latter compounds with $RR^1P-OR^2$ give new compounds of the invention:

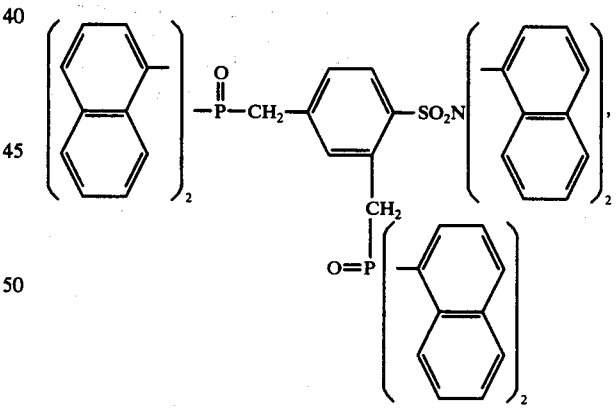

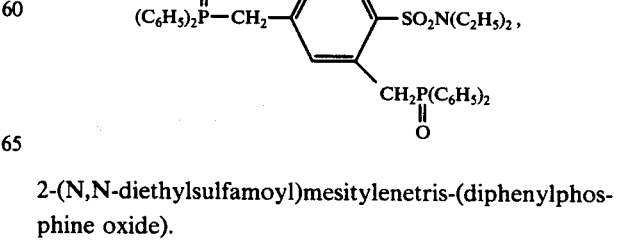

2-(N,N-diethylsulfamoyl)mesitylenetris-(diphenylphosphine oxide).

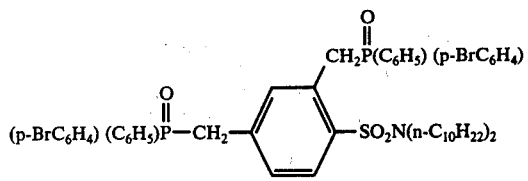
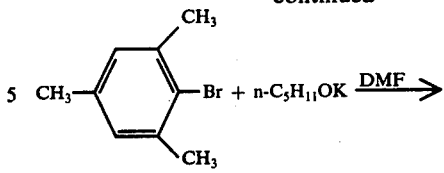

Other halomethyl substituted aromatic compounds II which can be used include the aryl sulfones where X is —SO₂R. Illustrative of the preparation of these sulfones is the reaction of benzenesulfonyl chloride and m-xylene in the presence of AlCl₃.

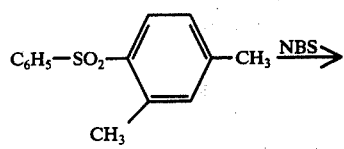

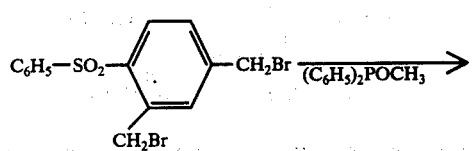

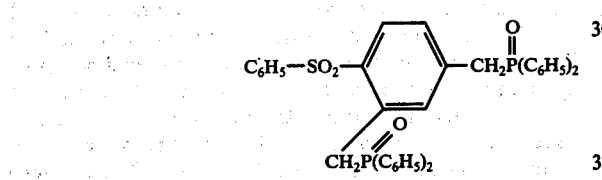

Still other halomethyl substituted aromatic compounds II which can be used include the aryl ethers and aryl thioethers where X is OR and SR, respectively. They have the formulas:

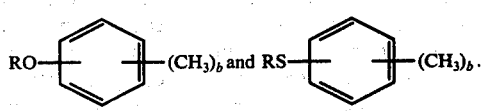

These compounds are available by reaction of a polymethylbenzene halide with an alkali metal salt of a thiol, alcohol or phenol, e.g.,

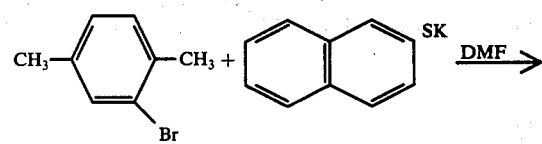

(DMF = dimethylformamide)

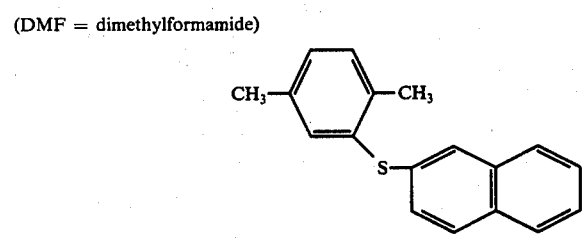

and

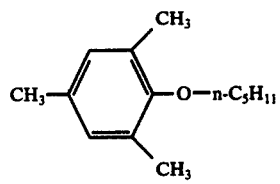

These ethers and thioethers by bromination as described above give the bromomethyl derivatives which are reactive with alkyl disubstituted phosphinites to give corresponding arylene disubstituted phosphine oxides, such as,

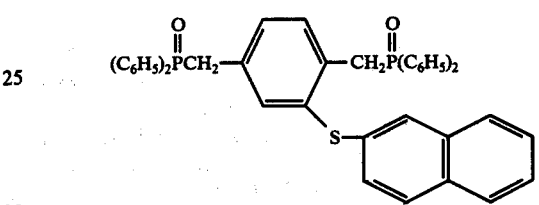

and

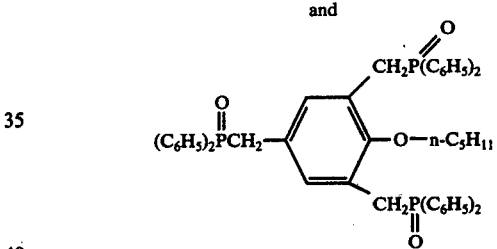

Oxidation of the thio compounds gives sulfoxides. Sulfones can also be obtained by further oxidation.

Specific compounds include within the scope of this invention obtained from previously described reactants are:

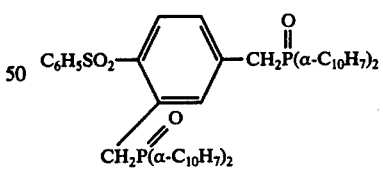

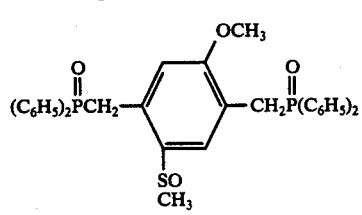

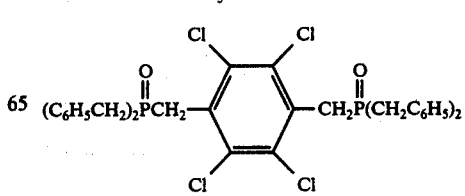

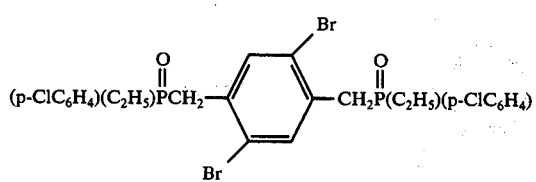

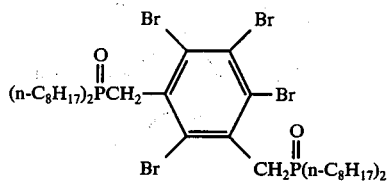

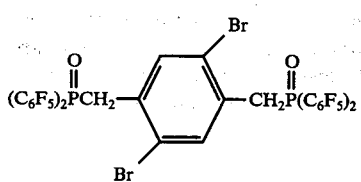

When 1-hexyl-2,4,6-tris(chloromethyl)benzene, 1,3,5-tris(chloromethyl)benzene, 1,2,4,5-tetrakis(bromomethyl)benzene, 1,2,3,4,5-pentakis(bromomethyl)benzene or hexakis(bromomethyl)benzene are substituted for 2,4,6-tris(chloromethyl)mesitylene in the procedure of Example 8, the respective products are:

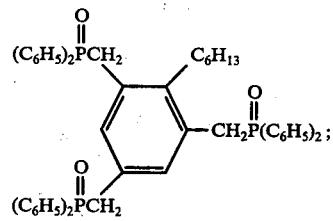

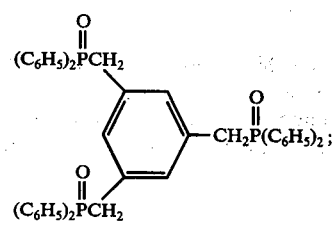

The use of the new compounds of this invention as flame retardants for polyolefins has been demonstrated by following the Underwriters Laboratory procedure (UL-94) in the following manner: Commercial polypropylene (28 g) was fluxed on a 2-roll mill (Junior Lab 3 × 8 inch rolls), 12 g of the flame-retardant additive was added to the resin band, and the mixture milled ca. 6 minutes, during which time five-to-ten "cuts" were made to enhance blending. The resin sheet was ground up in a Wiley mill. The resulting powder was molded into 5 × ½ × ⅛ inch flex bars using a laboratory scale injection mold.

The bars (five from each batch) were subjected to flammability testing. The bars were supported vertically. Each sample was ignited twice, $I_1$ and $I_2$, for 10 seconds with a Bunsen burner. After each ignition, there was no continued burning, i.e., the polymer was self-extinguishing. Even though all dripped molten polymer to cotton batting 12 inches below, the sample in only one of a series of five (using the compound of Example 4) did the cotton ignite. Compounds used in the test included those of Examples 1, 2, 4, and 8. In contrast to these results, when 1,2-xylylenebis-(diphenylphosphine oxide) was used in the same manner as a control, three of the five samples ignited the cotton. The data are presented in Table II.

Table II

| Example | Compound | No. | Time of $I_1$ (sec) | Burn Time (sec) | Time of $I_2$ (sec) | Burn Time (sec) | Drip? (yes/no) | Ignite cotton? (yes/no) |
|---|---|---|---|---|---|---|---|---|
| 1. | Br, CH₂P(O)φ₂, Br, Br, Br, CH₂P(O)φ₂ | 1 | 10 | — | 10 | — | yes | no |
| | | 2 | 10 | — | 10 | — | yes | no |
| | | 3 | 10 | — | 10 | — | yes | no |
| | | 4 | 10 | — | 10 | — | yes | no |
| | | 5 | 10 | — | 10 | — | yes | no |

Table II-continued

| Example | Compound | No. | Time of $I_1$ (sec) | Burn Time (sec) | Time of $I_2$ (sec) | Burn Time (sec) | Drip? (yes/no) | Ignite cotton? (yes/no) |
|---|---|---|---|---|---|---|---|---|
| 2. | φ₂P(O)CH₂–[C₆H₂(Br)₂]–CH₂P(O)φ₂ | 1 | 10 | — | 10 | — | yes | no |
| | | 2 | 10 | — | 10 | — | yes | no |
| | | 3 | 10 | — | 10 | — | yes | no |
| | | 4 | 10 | — | 10 | — | yes | no |
| | | 5 | 10 | — | 10 | — | yes | no |
| 4. | φ₂P(O)CH₂–[C₆Cl₄]–CH₂P(O)φ₂ | 1 | 10 | — | 10 | — | yes | yes |
| | | 2 | 10 | — | 10 | — | yes | no |
| | | 3 | 10 | — | 10 | — | yes | no |
| | | 4 | 10 | — | 10 | — | yes | no |
| | | 5 | 10 | — | 10 | — | yes | no |
| 8. | H₃C, CH₂P(O)φ₂, φ₂P(O)CH₂, CH₃, CH₃, CH₂P(O)φ₂ on benzene | 1 | 10 | — | 10 | — | yes | no' |
| | | 2 | 10 | — | 10 | — | yes | no |
| | | 3 | 10 | — | 10 | — | yes | no |
| | | 4 | 10 | — | 10 | — | yes | no |
| | | 5 | 10 | — | 10 | — | yes | no |
| Control | C₆H₄(CH₂P(O)φ₂)₂ | 1 | 10 | — | 10 | — | yes | yes |
| | | 2 | 10 | — | 10 | — | yes | yes |
| | | 3 | 10 | — | 10 | — | yes | no |
| | | 4 | 10 | — | 10 | — | yes | no |
| | | 5 | 10 | — | 10 | — | yes | yes |

In another test for flame retardancy, a mixture of 1 g of 2,5-dibromo-p-xylylenebis(diphenylphosphine oxide) and 9 g of powdered polyethylene terephthalate was dry-milled for 60 minutes. Two grams of the resulting mixed powder was pressed on a fiberglass cloth in a platen press at 280° C to obtain a glass-supported film. The film was cut into five strips which were suspended horizontally and ignited with a wooden match. The first half inch of burning was ignored. All five samples self-extinguished in 5–10 seconds after burning less than ¼ inch (about 0.025 in/sec). A control glass-supported polyethylene terephthalate film burned completely in 40 seconds (0.05 in/sec).

The compounds of this invention are also useful as flame retardants with many synthetic polymers including polyacrylonitrile; polyolefins such as polyethylene and polypropylene; polyesters such as polyethylene terephthalate; and polyamides such as polycaprolactam, polyamide from hexamethylenediamine and adipic acid, polyamide from bis(4-aminocyclohexyl)methane and dodecanedioic acid, and the like. They are generally incorporated in polymers by melt blending but can be mixed in powder or liquid form. Surface treatment of textiles also provides fire-retardant properties. In general, amounts of 1–25% by weight of the new phosphine oxides are admixed with the polymer for improvement in fire-retardant properties. Preferred results are obtained when 5–15% of the phosphine oxide is used.

The fire-retardant or flame-retardant property of a material refers to its resistance to burning and its capacity to be self-extinguishing when once ignited. Preferred compositions containing the compounds of this invention are those which when ignited by a flame are self-extinguishing when the source of that flame is removed.

Textiles include particularly those fabrics formed from fibers by weaving, knitting or non-woven techniques.

The embodiments of the invention in which an exclusive property or privilege is claimed are defined as follows:

1. A flame-retardant compound having the formula

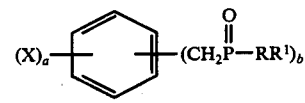

wherein

R and R¹ individually are alkyl, aryl or aralkyl of up to 10 carbon atoms having up to 5 chlorine, bromine or fluorine atoms;

X is $SO_2NH_2$, $SO_2NHR$ or $SO_2NR_2$, R being as defined above;

$a$ is 1 to 4; $b$ is 2 to 5; and $a + b$ is 3 to 6.

2. The compound of claim 1 which is 2-(N,N-diethylsulfamoyl)mesitylenetris(diphenylphosphine oxide).

3. A flame-retardant composition comprising a polymer selected from the group consisting of a polyolefin, polyester and polyamide and 1–25% by weight, based on the said polymer, of a compound of claim 1.

4. The composition of claim 3 in which the polymer is polypropylene.

5. The composition of claim 3 in which the polymer is polyethylene terephthalate.

6. The composition of claim 3 in which the polymer is polycaprolactam.

* * * * *